United States Patent [19]

Streicher

[11] Patent Number: 5,354,689
[45] Date of Patent: Oct. 11, 1994

[54] METHOD OF DETECTING ISOCYANATES

[75] Inventor: Robert P. Streicher, Cincinnati, Ohio

[73] Assignee: The United States of America as represented by the Department of Health and Human Services, Washington, D.C.

[21] Appl. No.: 59,810

[22] Filed: May 10, 1993

[51] Int. Cl.$^5$ ...................... G01N 21/64; G01N 31/22
[52] U.S. Cl. .................................. 436/109; 436/161; 436/172; 436/902
[58] Field of Search ............... 436/109, 171, 172, 902, 436/161

[56] References Cited

U.S. PATENT DOCUMENTS

| | | | |
|---|---|---|---|
| 2,636,032 | 4/1953 | Weston et al. | 544/380 |
| 3,800,044 | 3/1974 | Craig et al. | 424/330 |
| 3,896,133 | 7/1975 | Craig et al. | 260/293.62 |
| 4,128,513 | 12/1978 | Errede et al. | 521/50 |
| 4,792,551 | 12/1988 | Nelson et al. | 514/651 |
| 4,857,644 | 8/1989 | Abou-Gharbia | 544/295 |
| 4,954,416 | 9/1990 | Wright et al. | 430/281 |
| 5,101,059 | 3/1992 | Carpino et al. | 549/388 |

OTHER PUBLICATIONS

C. Purnell et al., *Methods for the Determination of Atmospheric Organic Isocyanates A Review*, Analyst, Aug. 10, 1985, vol. 110, pp. 893–905.

N. Kornblum et al., *A New Method for Protecting Amines*, J. Org. Chem, vol. 42, No. 2, 1977, pp. 399–400.

V. Dharmarajan et al., *Recent Developments in the Sampling and Analysis of Isocyanates in Air, Sampling and Calibration for Atmospheric Measurements*, ASTM STP 957 (American Society for Testing and Materials, Philadelphia, 1987) pp. 190–202.

S. Robertson, *Determination of Total Isocyanate Concentration in Air by Headspace Gas Chromatography*, Health and Safety Executive, Research and Laboratory Services Division, Section Paper (Jan., 1986).

J. Liu et al., *Photokinetics of the Fluorescence Quenching of 9-Methylanthracene by Piperazines*, Chemical Physics Letters, vol. 146, No. 5, May, 1988, pp. 382–386.

W. Wu et al., *Application of Tryptamine as a Derivatising Agent for Airborne Isocyanate Determination, Part 3. Evaluation of Total Isocyanates Analysis by High-performance Liquid Chromatography With Fluorescense and Amperometric Detection*, Analyst, vol. 115, Jun., 1990, pp. 801–807.

MDHS 25—*Methods For The Determination of Hazardous Substances: Organic Isocyanates in Air*, Health and Safety Executive: Occupational Medicine And Hygiene Laboratory, Mar. 1987.

K. Marcoli, *Microdetermination of Toluenediisocyanates in Atmosphere*, Analytical Chemistry, vol. 9, No. 4, 1957, pp. 522–558.

Hardy, H. L. et al., *Novel Reagent for the Determination of Atmospheric Isocyanates Monomer Concentrations*, (List continued on next page.)

Primary Examiner—David A. Redding
Attorney, Agent, or Firm—Leydig, Voit & Mayer, Ltd.

[57] ABSTRACT

The present invention provides for a method for detecting the presence of isocyanate in a sample by (a) contacting an isocyanate derivatizing reagent having the formula I $$R—R' \qquad (I)$$

wherein R is 9-anthracenylmethyl or a derivative thereof and R' is a radical having a single isocyanate-derivatizing functionality comprising a radical derived from a cyclic secondary amine with a sample under conditions suitable to the formation of a reaction product capable of detection and (b) detecting the presence or absence of the reaction product as an indication of the presence or absence of isocyanate in said sample. The present invention also provides a method of quantifying the total isocyanate presence by quantifying the reaction product.

18 Claims, No Drawings

OTHER PUBLICATIONS

*Analyst,* vol. 104, 1979, pp. 890–891.

Sango, C. et al., *A New Reagent for Determination of Isocyanates in Working Atmospheres by HPLC using UV or Fluorescence Detection, J. Liq. Chromatogr,* vol. 3(7), 1980, pp. 971–990.

Goldberg, P. S. et al., *Determination of Trace Atmospheric Isocyanate Concentrations by Reversed-Phase High-Performance Liquid Chromatography using 1-(-2-pyridyl)piperazine, J. Chromatogr.,* vol. 212, 1981, pp 93–104.

Warwick, C. J. et al., *Application of Electrochemical Detection to the Measurement of Free Monomeric Aromatic and Aliphatic Isocyanates in Air by High-Performance Liquid Chromatography, Analyst,* vol. 106, 1981, pp. 676–685.

Bagon, D. A., et al., *Evaluation of Total Isocyanate-in-Air Method Using 1-(2-Methoxyphenyl)piperazine and HPLC, Am. Ind. Hyg. Assoc. J.,* vol. 45(1), 1984, pp. 39–43.

METHOD OF DETECTING ISOCYANATES

TECHNICAL FIELD OF THE INVENTION

The present invention relates to the detection of isocyanates, particularly in air. The present invention further provides for a method to detect and quantify isocyanates in a sample.

BACKGROUND OF THE INVENTION

Isocyanates are a class of chemicals which are used in the production of a wide variety of chemical compounds. These chemical compounds are in turn incorporated into a vast number of products which are used in great quantities world-wide. Monoisocyanates are used as intermediates in the production of herbicides, crop protection agents, and antidiabetic pharmaceuticals, while long-chain aliphatic monoisocyanates are used for the surface treatment of textiles. Diisocyanates and polyisocyanates are intermediates in the manufacture of polyurethane materials. These materials include rigid foams for insulation, flexible foams for seating, and paints yielding durable finishes. In preparing these and other commercial products, manufacturers utilize the various species of isocyanates, both alone and in combination, in order to obtain the desired characteristics in the final product.

While isocyanates provide a great many benefits, their use is unfortunately accompanied by certain problems. One of the most serious of these is the effect of isocyanates on the human respiratory system. Upon inhalation, isocyanates act as respiratory irritants. Fortunately, in the short term, the symptoms resulting from isocyanate inhalation usually disappear after removal of the person from the contaminated environment. Repeated exposure to isocyanates over a prolonged period, however, can lead to progressive and permanent impairment of pulmonary function. This impairment manifests itself in the form of shortness of breath and increased stress on the heart. More seriously, a "sensitized" condition arises in approximately 5 percent of all persons exposed to isocyanates. In this condition, asthmatic symptoms present themselves almost immediately upon exposure to even relatively low concentrations of isocyanates, i.e., concentrations which do not affect those who are not sensitized to isocyanates.

Because of the serious adverse physiological effects associated with isocyanate inhalation, attention has been given to devising methods for the detection of isocyanates. Several of these methods are concerned with determining the concentration of particular airborne isocyanate species in an environment, while others are directed toward measuring the residual isocyanate monomer content in various isocyanate starting materials, e.g., bulk isocyanate prepolymers and the like. In addition, methods for determining the percentage of free isocyanate groups present in urethane-based polymers have also been developed. Although such methods are predominantly spectrophotometric or chromatography-based, polarography, potentiometry, dielectric constant determination, detector tubes, impregnated paper tapes, and coated piezoelectric crystals have also been used for this purpose. An overview of various methods presently available for the detection of isocyanate species in air is provided in Dharmarajan et al., "Recent Developments in the Sampling and Analysis of Isocyanates in Air, Sampling and Calibration for Atmospheric Instruments," *Am. Soc'y for Testing & Materials,* Spec. Tech. Pub. No. 957, pp. 190–202 (1987), and Purnell et al., "Methods for the Determination of Atmospheric Organic Isocyanates: A Review," *Analyst,* 110, 893–905 (1985).

While the detection and quantification of particular isocyanate species are important, it is also desirable that a method be able to detect and quantify the total number of isocyanate groups present in an environment, regardless of the particular isocyanate species which are present. This arises from the fact that the health risks mentioned previously may not occur only as a result of exposure to a single isocyanate species. In recognition of this, the United Kingdom has adopted an exposure standard for isocyanates which is based upon the total isocyanate groups present in an environment. Silk et al., *Ann. Occup. Hyg.,* 27 (4), 333-39 (1983).

One particular method which could conceivably be used to determine the total isocyanate groups present in a sample is described in Marcali, "Microdetermination of Toluenediisocyanates in Atmosphere," *Anal. Chem.,* 29 (4), 552–558 (1957). The method described in that article comprises initially hydrolyzing a toluenediisocyanate (TDI) monomer to prepare a derivative thereof, i.e., a toluenediamine (TDA). Diazotization of the TDA, and subsequent coupling of the stable diazo compound with N-1-naphthylethylenediamine, is then undertaken. This results in the production of a compound having a reddish-blue color, which compound may be measured spectrophotometrically to determine the isocyanate level.

This method was originally intended by its developers to enable the detection of trace quantities, i.e., down to 10–20 ppb, of particular isocyanate monomer species in air, namely toluenediisocyanates. However, in practice, it was discovered that the method was susceptible to interferences which subverted that goal. For example, it was found that TDA and any other aromatic amines present in the sample were also diazotized and bonded to the N-1-naphthylethylene diamine. As TDI is converted to TDA in the reaction scheme, TDA present in the air sample will result in a false positive reading for TDI. Moreover, the method possesses poor sensitivity (in the range of 20 ppb) relative to HPLC methods developed in the 1980's. Further, different isocyanates have different response factors. Accordingly, quantification of isocyanates can only be accomplished for those species for which the response factor is already known. In addition, mixtures of isocyanates for which the response factors are known cannot be accurately quantified without knowing their relative amounts. For example, 2,4-TDI and 2,6-TDI, which are typically found together in products, have different response factors. As such, obtaining an accurate measure of the total isocyanate species depends upon knowing the relative amount of each.

A method which has been used for detecting the total isocyanate presence in a sample involves derivatizing isocyanates by forming ureas therefrom using 1-(2methoxyphenyl)piperazine (MOPP):

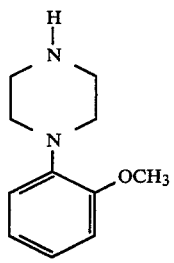

The resulting ureas are then analyzed using high performance liquid chromatography (HPLC) equipped with ultraviolet (UV) and electrochemical (EC) detectors. Isocyanate-derived peaks are identified on the basis of their UV/EC response ratio and all such peaks are quantified using an isocyanate monomer standard. The total airborne isocyanate concentration is then calculated from the sum of all isocyanate-derived HPLC peaks as described in "Health and Safety Executive: MDHS 25, Methods for the Determination of Hazardous Substances: Organic Isocyanates in Air," *Health & Safety Executive/Occupational Safety and Hygiene Laboratory* (1987).

An evaluation of this method, however, has revealed that neither detector (UV or EC) response was found to be proportional to the number of derivatized isocyanate groups present in model urethane oligomers. See Streicher et al ,. "Investigation of the Ability of MDHS 25 to Determine Urethane-Bound Isocyanate Groups," presented at the American Industrial Hygiene Conference and Exposition, Boston, Mass., May 30–June 5, 1992. This non-proportional response makes the method unreliable in terms of both its ability to correctly identify isocyanate species and inaccurate in its quantification of such species.

Another reaction scheme which has been considered in an effort to quantify the total isocyanates in a sample, e.g., air, involves passing the air through an impinger containing propanol under favorable conditions, wherein the isocyanate species reacts with propanol to yield their respective propyl carbamates. The excess propanol is then removed from the reacted mixture, the carbamate is subsequently hydrolyzed, and the resulting propanol is analyzed. The amount of propanol provides a quantification of the total isocyanates present. See Robertson, "Determination Of Total Isocyanate Concentrations In Air By Headspace Gas Chromatography," *Section Paper of the Health & Safety Executive, Research & Laboratory Services Division* (1986).

This methodology, however, suffers from at least three drawbacks. First, since the derivatizing reagent and the analyte are identical (propanol), the derivatizing reagent may introduce inaccuracies into the analysis if it is not completely removed after the formation of the carbamate. Secondly, the conditions required to regenerate the propanol from the carbamate are relatively harsh, and, thirdly, the rate of the hydrolysis reaction varies substantially with the various isocyanate species.

Yet another method utilizes tryptamine:

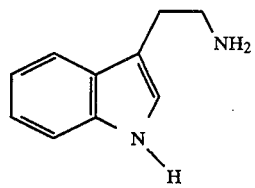

as the derivatizing reagent for the isocyanate. After derivatization, HPLC with fluorescence and electrochemical detection in series is employed. See Wu et al., "Application of Tryptamine as a Derivatizing Reagent for the Determination of Airborne Isocyanates: Part 3. Evaluation of Total Isocyanates Analysis by High-Performance Liquid Chromatography With Fluorescence and Amperometric Detection," *Analyst*, 115, 801–807 (1990).

While this method provides a relatively higher degree of selective detection and a less-variable response factor than the method which uses 1-(2-methoxyphenyl)piperazine, there are certain aspects that could be improved upon. For example, a reagent which reacts with isocyanates faster than tryptamine would be desirable. This is because the more reactive the reagent is with an isocyanate, the smaller is the problem of losses of isocyanates to side reactions after the isocyanate is collected but prior to derivatization. Secondly, a reagent that provides a greater detector response than tryptamine would enable determination of the quantity of isocyanates at lower concentration levels. Finally, a reagent that yields derivatized isocyanates whose detector responses vary less than those derived from tryptamine would enable a more accurate identification and quantification of isocyanate species.

Other reagents have also been utilized to derivatize isocyanates, rendering them analyzable. For example, 9-(methylaminomethyl)anthracene (MAMA):

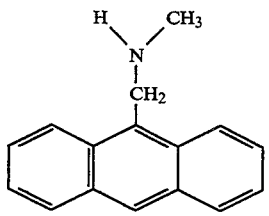

and 1-(2-pyridyl) piperazine:

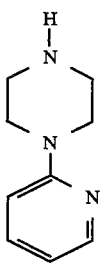

have been used in an effort to determine the presence of particular isocyanate species present in a sample as opposed to the total species present therein. With respect to MAMA, this reagent could conceivably be used to detect total isocyanate species present in a sample. However, in practice, the response of the derivatized isocyanate formed thereby would be influenced by the physical proximity of the isocyanate functionality, thus introducing error into attempts to quantify the total isocyanate presence. In addition, it would be advantageous if a means were provided by which isocyanates could be derivatized at a rate which is faster than that provided by MAMA.

However, it is believed that MAMA and 1-(2-pyridyl)piperazine have not been used to determine the total amount of isocyanates present in a sample. Moreover, and as regarding MOPP, it would be advantageous if a means were available whereby certain properties, e.g., the rate of reaction with isocyanates and detectability, could be improved over that provided by MOPP.

Thus, there exists a need for a method which will provide a relatively safe and simple means for the quantitative detection of all isocyanate species present in a sample at low concentrations. Moreover, there exists a need for a method which minimizes the problems associated with the detection of isocyanates due to their instability.

It is therefore an object of the present invention to provide a method which is able to derivatize an isocyanate functionality and thereby provide a means by which the presence of low amounts of isocyanates can be detected both readily and with a high degree of accuracy. Another object is to provide a means for quantifying the total presence of isocyanate species in a sample, regardless of the particular species present in the sample. A related object of the present invention is to provide a method which provides for the derivatization of isocyanates at a relatively rapid rate as compared to known methods. A further object of the present invention is to provide a method wherein the reagents are analytically distinguishable from the reaction product which is analyzed to determine the presence of isocyanates, i.e., the analyte.

These and other objects and advantages of the present invention, as well as additional inventive features, will be apparent from the description of the invention provided herein.

BRIEF SUMMARY OF THE INVENTION

The present invention involves a method for detecting the presence of isocyanate in a sample by (a) contacting an isocyanate derivatizing reagent having the formula I

R—R'    (I), wherein R is 9-anthracenylmethyl or a derivative thereof and R' is a radical having a single isocyanate-derivatizing functionality comprising a cyclic secondary amine with a sample under conditions suitable for the formation of a reaction product capable of detection and (b) detecting the presence or absence of the reaction product as an indication of the presence or absence of isocyanates in said sample.

The present invention also provides for the quantification of the reaction products as an indication of the total quantity of the isocyanate in the sample.

The present invention further provides most preferred methods for isocyanate detection. Specifically, these methods utilize the isocyanate derivatizing reagent wherein R is 9-anthracenylmethyl and R' is 1,4-piperazinyl or 4,4'-bipiperidinyl. In such a case, the reagent of formula I will have the structure of formula II

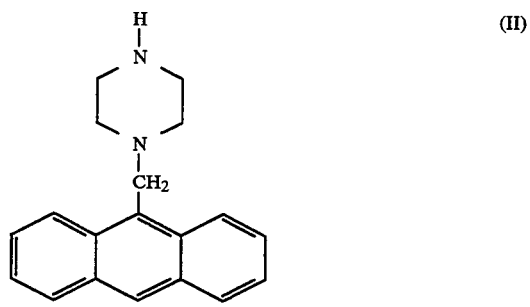

when R' is 1,4-piperazinyl and the structure of formula III

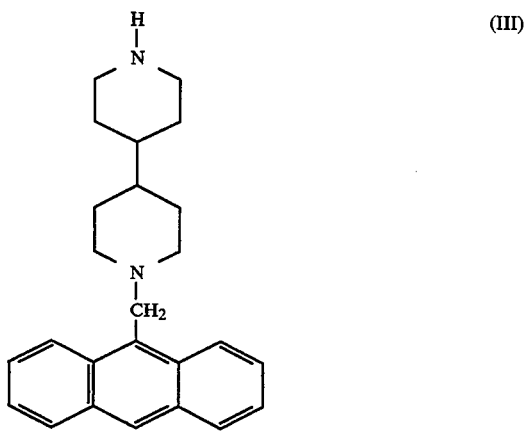

when R' is 4,4'-bipiperidinyl.

The present inventive methods are useful in the detection and quantification of a variety of isocyanate species in a wide variety of samples, and are particularly well-suited to the detection of isocyanates in air.

DETAILED DESCRIPTION OF THE PREFERRED EMBODIMENTS

The present invention provides for a method for detecting the presence of and quantifying isocyanate in a sample.

Isocyanates are compounds which contain the functional group —N=C=O and, therefore, have the formula R"—N=C=O, wherein R" may be any radical containing at least one carbon atom. The present inventive method comprises (a) contacting an isocyanate derivatizing reagent having the formula I

R—R'    (I), wherein R is 9-anthracenylmethyl or a derivative thereof and R' is a radical having a single isocyanate-derivatizing functionality comprising a cyclic secondary amine with a sample under conditions suitable for the formation of a reaction product capable of detection and (b) detecting the presence or absence of the reaction product as an indication of the presence or absence of isocyanate in the sample. While the present inventive method may be used solely to detect the presence of isocyanate in a sample, the method may also be used to quantify the isocyanate in a sample by quantifying the amount of reaction product, which is an indication of the quantity of isocyanate in the sample.

The reaction product in accordance with the present inventive method will typically be a derivatized isocyanate having the formula IV

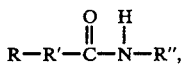

$$R-R'-\overset{O}{\underset{\|}{C}}-\overset{H}{\underset{|}{N}}-R'',\quad (IV)$$

wherein R" is derived from an isocyanate having the formula R"—N=C=O and is a radical containing at least one carbon atom. This derivatized isocyanate may be detected and quantified in accordance with the present invention as an indication of the presence or absence of isocyanate and, if present, the quantity of isocyanate, using conventional methods.

Using any of the derivatizing reagents of the present invention, the formation of a derivatized isocyanate is dependent on the presence of isocyanate in the sample. This, in turn, allows the presence or absence of the derivatized isocyanate to be detected as an indication of the presence or absence of isocyanate in the sample. Moreover, since the quantity of the derivatized isocyanate is directly related to the quantity of isocyanate in the original sample, the quantity of isocyanate can be determined by quantifying the thus formed derivatized isocyanate.

As regarding the isocyanate derivatizing reagent, R is 9-anthracenylmethyl or a derivative thereof and R' is a radical which includes a cyclic secondary amine, i.e., the amino nitrogen being in a ring structure, the ring structure in turn being part of the radical. Advantageously, R' is a radical which is derived from a cyclic diamine, i.e., the radical contains one or more ring structures wherein two nitrogen atoms are in the ring structure(s), one of which bonds to 9-anthracenylmethyl (or a derivative thereof) and the other being free to bond with an isocyanate functionality. Preferably, R' is a radical derived from a cyclic, symmetric secondary/secondary diamine, i.e., the radical contains one or more ring structures wherein two nitrogen atoms are in the ring structure(s), one of the nitrogen atoms bonding with 9-anthracenylmethyl thereby forming a tertiary nitrogen, the second nitrogen being free to bond with an isocyanate functionality. The formation of the tertiary nitrogen prevents that nitrogen from bonding with an isocyanate functionality. Further, the nitrogen atoms are located symmetrically in the ring structure(s). This provides for the formation of a single product upon coupling of the diamine with the 9-anthracenylmethyl radical, regardless of which nitrogen is bonded to the 9anthracenylmethyl radical. Most preferably, then, R' is 1,4-piperazinyl, 4,4'-bipiperidinyl, or a derivative thereof.

The compounds defined as R' that are utilized in the present invention, and particularly those which are advantageously utilized, further provide a "buffer" between the 9-anthracenylmethyl group and the bound isocyanate functionality. The presence of the aforesaid "buffer" is believed to assist in the elimination of the influence that the isocyanate functionality would normally have upon the detector response factor. This results in more accurate identification and quantification of the derivatized isocyanates and, hence, the total isocyanate presence in a sample.

With regard to the reagent as a whole, preferably R is 9-anthracenylmethyl and R' is 1,4-piperazinyl, as opposed to derivatives thereof, although many such derivatives may be satisfactorily used in the context of the present inventive method.

As stated previously, the functionality R possesses the ability to be detected at low levels by conventional apparatuses, advantageously using HPLC with two detectors in series, preferably UV and fluorescence. Typically, that functionality, in combination with the aforementioned apparatus, should provide the derivatized isocyanate with the ability to be detected at a level which is lower than that offered through use of the tryptamine methodology.

The derivative of 9-anthracenylmethyl may be any suitable derivative and advantageously is 9-anthracenylmethyl with at least one substituent thereon. It is desirable that any such substituents have relatively small electronic effects in order to minimize any adverse effect they might have on the absorbance or fluorescence properties. Examples of such substituents include alkyls.

R' is a radical which contains a single isocyanate-derivatizing functionality, i.e., a functionality which will derivatize only a single isocyanate functionality. This single functionality is significant if one desires to determine the quantity of isocyanate functionalities present in a sample. This aspect of the invention will be more fully explained below in connection with the discussion regarding the applicable analytical methods. The isocyanate-derivatizing functionality in accordance with the present invention comprises a cyclic secondary amine.

As mentioned previously, R' most preferably will comprise 1,4-piperazinyl, 4,4'-bipiperidinyl or a derivative thereof. The derivative may be any suitable derivative, with the preferred derivative comprising 1,4-piperazinyl with at least one substituent thereon. Although substituents may be located at any position on the ring, such substituents are preferably located on the piperazine ring at the 2 and/or 6 positions. While substituents could also be placed on the piperazine ring at the 3 and/or 5 positions, these substituents could result in undesirable steric hindrance and electronic effects which could adversely affect the rate and course of the reaction of the isocyanate derivatizing reagent with the isocyanate in the sample. Thus, while a substituent on the piperazine ring may be any suitable radical, such a substituent is preferably a radical with relatively small electronic effects, such as an alkyl.

One of the most preferred embodiments of the present invention involves the use of an isocyanate derivatizing reagent of formula I wherein R is 9-anthracenylmethyl and R' is 1,4-piperazinyl. Under such circumstances, the isocyanate derivatizing reagent is 1-(9-anthracenylmethyl)piperazine or MAP and has the formula II

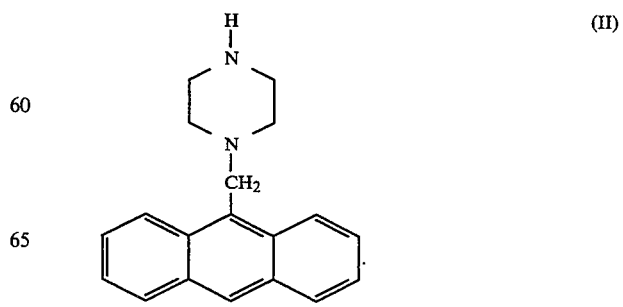

Another of the most preferred embodiments of the present invention involves the use of an isocyanate derivatizing reagent of formula I wherein R is 9-anthracenylmethyl and R" is 4,4'-bipiperidinyl. Under such circumstances, the derivatizing reagent is 1-(9-anthracenylmethyl)- 4,4'-bipiperdine and has the formula III

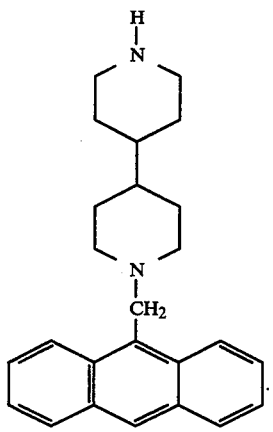

The reaction of the isocyanate derivatizing reagent of formula II with isocyanates of formula R"—N=C=O results in the preparation of derivatized isocyanates of formula V

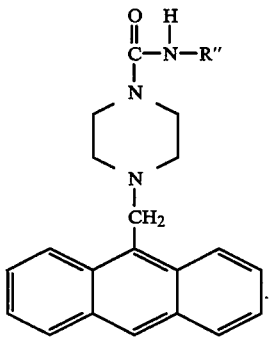

The detection and quantification of the reaction products, i.e., derivatized isocyanates, may be performed in any suitable manner. Since the 9-anthracenylmethyl group absorbs UV radiation very strongly at 254 nm and, further, fluoresces strongly, the present invention allows for the very reliable detection and quantification of the isocyanate reaction products resulting from the use of an isocyanate derivatizing reagent in accordance with the present invention.

The present inventive method may be carried out on any suitable sample and is particularly well-suited to the detection and quantification of isocyanates in air. In this respect, a sample, such as air, is contacted with a suitable medium, such as an aprotic organic solvent, which solvent contains the derivatizing reagents of the present invention. Each of the isocyanate functionalities present on the isocyanate species react with a single molecule of derivatizing reagent under conditions suitable for the formation of derivatized isocyanates, e.g., at ambient temperature and pressure. Typically, impingers or bubblers containing the aforesaid solutions of derivatizing reagents, reagent-coated filters, and reagent-coated sorbents are used as means by which said derivatizing reagents can be exposed to the sample. See, e.g., the Dharmarajan and Purnell articles cited herein.

The present invention is particularly well-suited to the detection and quantification of isocyanate inasmuch as the each isocyanate functional group present in a sample, irrespective of the particular isocyanate species, i.e., irrespective of the nature of R" in the isocyanate R"—N=C=O, reacts with one molecule of isocyanate derivatizing reagent of formula I to form one equivalent of derivatized isocyanate. The detection and quantification of the derivatized isocyanate prepared from the reagent of formula I or, more preferably, from the reagent of formula II, provides for the detection and quantification of the isocyanates present in the original sample.

Any analytical procedure which provides for the detection and quantification of a reaction product indicative of isocyanate presence and quantity can be used. Analysis is preferably undertaken using HPLC with two detectors in series, preferably UV and fluorescence. When this procedure is undertaken, the sample solution, which contains the reaction product, will be passed through a silica gel solid phase extraction cartridge and the MAP-derivatized isocyanate species eluted with an appropriate solvent. Thereafter, at least a portion of the eluted sample would then be injected into an HPLC with UV and fluorescence detectors in series.

Desirable qualities of the elution solvent are: (1) that it be sufficiently volatile to enable facile sample concentration, (2) that it be suitable for injection into a reversed-phase HPLC system, (3) that it does not absorb radiation strongly at the wavelength used to detect the analytes, and (4) that it elutes the MAP-derivatized isocyanate species before the elution of any unreacted MAP. This last requirement is important because the quantity of MAP present in the sample is likely to far outweigh the quantity of MAP-derivatized isocyanates. If the MAP is introduced onto the analytical HPLC column, the mobile phase has to be sufficiently weak to prevent the MAP from interfering with the analytes. This results in lengthy analysis times. However, if the MAP were already removed, as is proposed here, a much stronger HPLC mobile phase could be implemented, reducing analysis time and improving the detection and quantification of isocyanate oligomers. The ability of a solvent to adequately separate MAP-derivatized isocyanates from unreacted MAP can be examined using thin-layer chromatography (TLC) with silica gel plates. By introducing the MAP-derivatized isocyanates and unreacted MAP onto the plates and developing with the elution solvent under examination, the relative extent of migration of the MAP-derivatized isocyanates and the unreacted MAP give a good indication of the ability of the solvent to selectively elute the former from the silica gel solid phase extraction cartridge. One example of a solvent useful in effecting this separation is methyl acetate.

The present invention has a number of advantages over prior art techniques for detecting and quantifying isocyanates. In particular, the isocyanate derivatizing reagent of formula II reacts with phenyl isocyanate slightly faster than 1-(2-methoxyphenyl)piperazine and about three times faster than tryptamine under the same conditions. Moreover, while the fluorescence detection response factor of several tryptamine-derivatized isocyanates was found to vary with a standard deviation of 16 percent, the UV response of the same isocyanates derivatized using the isocyanate derivatizing reagent of formula II was found to vary with a standard deviation of only 1.6 percent. Further, the average response of isocyanates derivatized using the isocyanate derivatizing reagent of formula II on a fluorescence spectrophotometer was found to be 32 times greater than isocyanates derivatized using tryptamine.

The following examples further illustrate the present invention but, of course, should not be construed in any way as limiting its scope.

EXAMPLE 1

This example illustrates a procedure for preparing the isocyanate derivatizing reagent of formula II, i.e., 1-(9-anthracenylmethyl)piperazine, which is known as MAP.

Over the course of 30 minutes, a solution of 2.74 mmole of 9-(chloromethyl)anthracene in 100 ml acetonitrile was added in a dropwise manner to a solution of 27.2 mmoles of piperazine and 13.7 mmole of triethylamine in 100 ml acetonitrile. After allowing this to react overnight, the acetonitrile was removed by rotary evaporation.

The residue was dissolved in 100 ml toluene, and the insoluble portion of the residue was dissolved in 100 ml of water. The toluene and water solutions were then shaken together with the remaining aqueous phase being discarded thereafter. The toluene solution was then extracted twice with water, and the toluene solution and a small amount of precipitate were passed through a fritted-glass filter, with the filter being rinsed with 30 ml of toluene. The rinse was combined with the toluene extract, and the volume reduced to 30 ml by rotary evaporation.

The toluene was then placed in a sublimation apparatus and heated to 90° C. while being swept with a stream of nitrogen until dry. The apparatus was submerged in a wax bath at 135° C., and a vacuum of about 200 mtorr applied. Sublimation was continued until the quantity of residue in the base of the apparatus remained unchanged. The sublimed material was rinsed from the cold finger with a minimal amount of toluene, and the solution was returned to the cleaned sublimation apparatus. The toluene was then evaporated, and the residue again sublimed as before. The quantity of product obtained was 2.43 mmole (89% yield).

EXAMPLE 2

This example illustrates the contemplated use of the present inventive method to detect and quantify isocyanates in a sample of air using the isocyanate derivatizing reagent of Example 1.

MAP is dissolved in toluene, or possibly a less volatile non-polar organic solvent, at a concentration of about 1 mg/mL. This solution is then placed in an impinger. The air being sampled is passed through the impinger at a rate of about 1 L/min. After the desired amount of air has been sampled, the solution should be transferred to a screw-cap vial and shipped to the analytical laboratory. The sample solution would then be passed through a silica gel solid phase extraction cartridge, using pentane to displace any remaining impinger solvent, and the MAP-derivatized isocyanate species eluted with an appropriate solvent, the characteristics of which were previously discussed. Methyl acetate is one example of a solvent that can be used in effecting this separation. An internal standard, such as 2-ethylanthracene, would be added at this point and the sample then concentrated with a gentle stream of nitrogen, if desired. A portion of this sample should, at this point, be injected into an HPLC with UV and fluorescence detectors in series. Compounds in the chromatogram would be recognized as MAP derivatives by examining their UV/fluorescence detector response ratios. The derivatives would be quantified using their UV response, the UV response of the internal standard, and the known ratio of response factors for the internal standard and the MAP-derivatized isocyanate monomer.

All of the references cited herein are hereby incorporated in their entireties by reference.

While this invention has been described with an emphasis upon a preferred embodiment, it will be obvious to those of ordinary skill in the art that variations of the preferred methods and compounds may be used and that it is intended that the invention may be practiced otherwise than as specifically described herein. Accordingly, this invention includes all modifications encompassed within the spirit and scope of the invention as defined by the following claims.

What is claimed is:

1. A method for detecting the presence of isocyanate in a sample, which method comprises:
   (a) contacting an isocyanate derivatizing reagent having the formula I

wherein R is 9-anthracenylmethyl or a derivative thereof and R' is a radical having a single isocyanate-derivatizing functionality comprising a cyclic secondary amine with a sample under conditions suitable for the formation of a reaction product capable of detection, and
   (b) detecting the presence or absence of said reaction product as an indication of the presence or absence of isocyanate in said sample.

2. The method of claim 1, wherein said reaction product is quantified as an indication of the quantity of isocyanate in said sample.

3. The method of claim 2, wherein R' is a radical derived from a cyclic diamine.

4. The method of claim 3, wherein R' is a radical derived from a cyclic symmetric secondary/secondary diamine.

5. The method of claim 4, wherein R' is 1,4-piperazinyl, 4,4'-bipiperidinyl, or a derivative thereof.

6. The method of claim 5, wherein R' is 1,4-piperazinyl or a derivative thereof.

7. The method of claim 6, wherein R is 9-anthracenylmethyl and R' is 1,4-piperazinyl.

8. The method of claim 1, wherein said reaction product is a derivatized isocyanate having the formula IV

wherein R" is derived from said isocyanates having formula R"—N=C=O and is a radical containing at least one carbon atom.

9. The method of claim 8, wherein R' is a radical derived from a cyclic diamine.

10. The method of claim 9, wherein R' is a radical derived from a cyclic symmetric secondary/secondary diamine.

11. The method of claim 10, wherein R' is 1,4-piperazinyl, 4,4'-bipiperidinyl, or a derivative thereof.

12. The method of claim 11, wherein R' is 1,4-piperazinyl or a derivative thereof.

13. The method of claim 12, wherein R is 9-anthracenylmethyl and R' is 1,4-piperazinyl.

14. The method of claim 8, wherein said reaction product is a derivatized isocyanate having the formula V

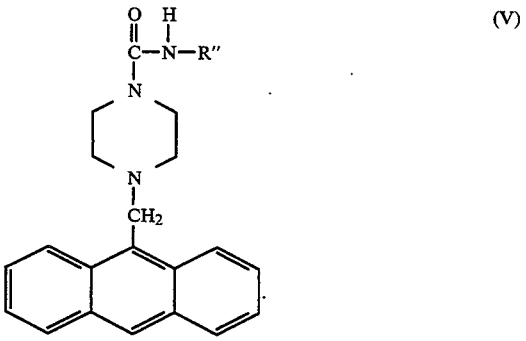

15. The method according to claim 14, wherein the derivatized isocyanate of formula IV is quantified as an indication of the quantity of isocyanates in said sample.

16. The method of claim 1, wherein the presence or absence of reaction product in the sample is detected using HPLC with UV and fluorescence detectors in series.

17. The method of claim 16, wherein presence or absence of reaction product in the sample is detected by examining the UV/fluorescence detector response ratio.

18. The method of claim 16, further comprising determining the UV response of an internal standard, wherein said reaction product is quantified by examining the UV response of said product, the UV response of the internal standard, and the known ratio of response factors for the internal standard and said reaction product.

* * * * *